US012614639B2

(12) United States Patent
Stenzler et al.

(10) Patent No.: US 12,614,639 B2
(45) Date of Patent: Apr. 28, 2026

(54) METHOD FOR TREATING A PATIENT WITH RESPIRATORY ILLNESS

(71) Applicant: Monitored Therapeutics, Inc., Dublin, OH (US)

(72) Inventors: Alex Stenzler, Long Beach, CA (US); Mac Liaw, Westerville, OH (US); Martin Stegenga, Dublin, OH (US); Michael Taylor, Dublin, OH (US)

(73) Assignee: Monitored Therapeutics, Inc., Dublin, OH (US)

( * ) Notice: Subject to any disclaimer, the term of this patent is extended or adjusted under 35 U.S.C. 154(b) by 205 days.

(21) Appl. No.: 18/630,289

(22) Filed: Apr. 9, 2024

(65) Prior Publication Data

US 2024/0363253 A1      Oct. 31, 2024

Related U.S. Application Data

(60) Provisional application No. 63/498,645, filed on Apr. 27, 2023.

(51) Int. Cl.
*G16H 50/30* (2018.01)
*A61B 5/00* (2006.01)
(Continued)

(52) U.S. Cl.
CPC ........... *G16H 50/30* (2018.01); *A61B 5/0022* (2013.01); *A61B 5/0205* (2013.01); *A61B 5/744* (2013.01);
(Continued)

(58) Field of Classification Search
CPC ........ G16H 50/20; G16H 50/50; G16H 20/00; G16H 50/00; G06N 20/00; G06N 3/02; G06N 3/006; G09B 23/28
See application file for complete search history.

(56) References Cited

U.S. PATENT DOCUMENTS

2020/0135334 A1 * 4/2020 Rajasekhar ............ G06N 3/084
2024/0050689 A1 * 2/2024 English ................. A61M 21/00

* cited by examiner

*Primary Examiner* — Joseph D Burgess
(74) *Attorney, Agent, or Firm* — Riverside Law LLP

(57) ABSTRACT

A method for treating a patient with respiratory illness is described according to one embodiment. The method includes the steps of receiving a set of screening spirometry test data measured by a spirometer, generating a first patient performance score based on the received set of screening spirometry test data, generating one of a first high alert when the first patient performance score crosses a first threshold and a first low alert when the first patient performance score fails to cross the first threshold, receiving a set of at-home physiological test data, generating a second patient performance score based on the received set of at-home physiological test data, generating one of a second high alert when the second patient performance score crosses a second threshold and a second low alert when the second patient performance score fails to cross the second threshold, receiving a set of at-home patient survey data entered by the patient, generating a third patient performance score based on the received set of at-home patient survey data, and generating one of a third high alert when the third patient performance score crosses a third threshold and a third low alert when the third patient performance score fails to cross the third threshold.

22 Claims, 6 Drawing Sheets

(51) Int. Cl.

| | |
|---|---|
| *A61B 5/0205* | (2006.01) |
| *G16H 10/20* | (2018.01) |
| *G16H 10/60* | (2018.01) |
| *G16H 20/10* | (2018.01) |
| *G16H 80/00* | (2018.01) |
| *A61B 5/021* | (2006.01) |
| *A61B 5/087* | (2006.01) |
| *A61B 5/1455* | (2006.01) |

(52) U.S. Cl.

CPC ............. *A61B 5/746* (2013.01); *G16H 10/20* (2018.01); *G16H 10/60* (2018.01); *G16H 20/10* (2018.01); *G16H 80/00* (2018.01); *A61B 5/021* (2013.01); *A61B 5/0871* (2013.01); *A61B 5/14551* (2013.01)

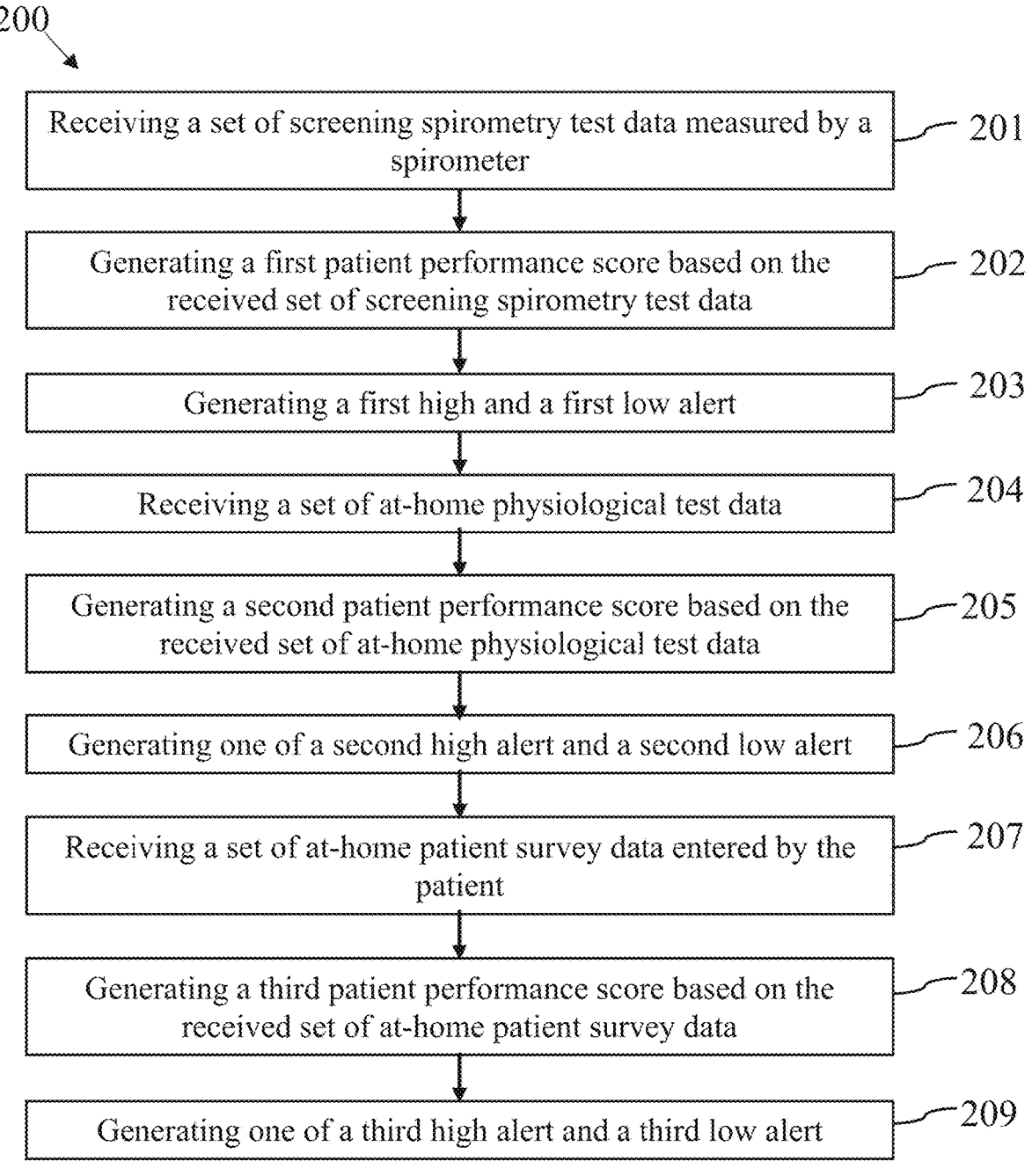

200

| | |
|---|---|
| Receiving a set of screening spirometry test data measured by a spirometer | 201 |
| Generating a first patient performance score based on the received set of screening spirometry test data | 202 |
| Generating a first high and a first low alert | 203 |
| Receiving a set of at-home physiological test data | 204 |
| Generating a second patient performance score based on the received set of at-home physiological test data | 205 |
| Generating one of a second high alert and a second low alert | 206 |
| Receiving a set of at-home patient survey data entered by the patient | 207 |
| Generating a third patient performance score based on the received set of at-home patient survey data | 208 |
| Generating one of a third high alert and a third low alert | 209 |

Fig. 2

METHOD FOR TREATING A PATIENT WITH RESPIRATORY ILLNESS

CROSS-REFERENCE TO RELATED APPLICATIONS

This application claims priority to U.S. Provisional Patent Application No. 63/498,645 filed Apr. 27, 2023 incorporated herein by reference in its entirety.

BACKGROUND OF THE INVENTION

Respiratory illness is a problem that affects a significant part of the US and world population. Specifically, COPD is underdiagnosed with an estimated 32 million people in the US suffering from its negative side effects. A significant portion of primary care providers (PCPs) do not perform spirometry in their offices to report on patient's respiratory wellness. This is caused by a concern with cost of the necessary equipment, but more importantly, the cost or absence of trained staff to use such equipment or specialize in respiratory health. Furthermore, current PCPs tend to lack comfort with interpreting lung function tests. Because of this, patients presenting with symptoms of issues in respiratory wellness will be referred to a specialist. These specialists are then burdened by patients with mild disease that do not need their involvement in the patient's care. Furthermore, specialists don't have the infrastructure in place to coordinate with PCPs to manage the patients that do need their skills.

A method for reliably and effectively expanding home monitoring technology and pushing duties from the specialist to the PCP would. Embodiments of the method described herein satisfies that need.

SUMMARY OF THE INVENTION

In one embodiment, a method for treating a patient with respiratory illness, includes the steps of receiving a set of screening spirometry test data measured by a spirometer; generating a first patient performance score based on the received set of screening spirometry test data; generating one of a first high alert when the first patient performance score crosses a first threshold and a first low alert when the first patient performance score fails to cross the first threshold; receiving a set of at-home physiological test data; generating a second patient performance score based on the received set of at-home physiological test data; generating one of a second high alert when the second patient performance score crosses a second threshold and a second low alert when the second patient performance score fails to cross the second threshold; receiving a set of at-home patient survey data entered by the patient; generating a third patient performance score based on the received set of at-home patient survey data; and generating one of a third high alert when the third patient performance score crosses a third threshold and a third low alert when the third patient performance score fails to cross the third threshold. In one embodiment, at least one of the first, second and third thresholds are set by an artificial intelligence module. In another embodiment, at least one of the first, second and third patient performance scores are calculated based on input from an artificial intelligence module. In one embodiment, the received set of at-home physiological test data is measured from a spirometer. In one embodiment, the first or second low alert generates a communication transmitted to a primary care physician. In one embodiment, the first or second high alert generates a communication transmitted to a respiratory specialist. In one embodiment, the third performance score low alert generates a communication transmitted to the patient and or the physician. In one embodiment, the third performance score high alert generates a communication transmitted to the patient and at least one of a primary care physician and a respiratory specialists. In one embodiment, the second threshold is based on input provided by at least one of a primary care physician and or a respiratory specialist. In one embodiment, the method further comprises providing a physiological measurement device configured to measure patient physiological data remotely, receiving a set of at-home physiological measurement data measured by the physiological measurement device, and generating the second patient performance score further based on the received set of at-home physiological measurement data. In another embodiment, the physiological measurement device includes a pulse oximeter. In one embodiment, the physiological measurement device includes a spirometer. In one embodiment, the physiological measurement device includes a blood pressure monitor. In one embodiment, the physiological measurement device includes a weight measurement device. In one embodiment, the physiological measurement device is configured to upload the patient test data to a remote server and generate a clinical alert by comparing the patient test data to a clinical threshold generated by the artificial intelligence program. In another embodiment, the step of generating a third patient performance score is further based on survey data generated by the patient. In one embodiment, the method further comprises instructing the patient to perform a breathing maneuver via an avatar. In one embodiment, the method further comprises instructing the patient to repeat a breathing maneuver via an avatar based on a previous spirometer measurement. In one embodiment, the method includes generating a Zscore for the patient and generating an alert when it falls below a Zscore threshold, wherein a reference population for generating the Zscore is solely based on previous measurements from the patient only. In one embodiment, the Zscore threshold is based on a patient-specific baseline. In one embodiment, the method includes generating a Zscore for the patient and generating an alert when it falls below a Zscore threshold a plurality of times over a plurality of days. In one embodiment, crossing the first or second threshold comprises crossing above the threshold. In one embodiment, crossing the first or second threshold comprises crossing below the threshold.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 2 is a flow chart for a method for treating a patient with respiratory illness implemented in a suitable computing environment, according to one embodiment.

DETAILED DESCRIPTION

Figure 1:
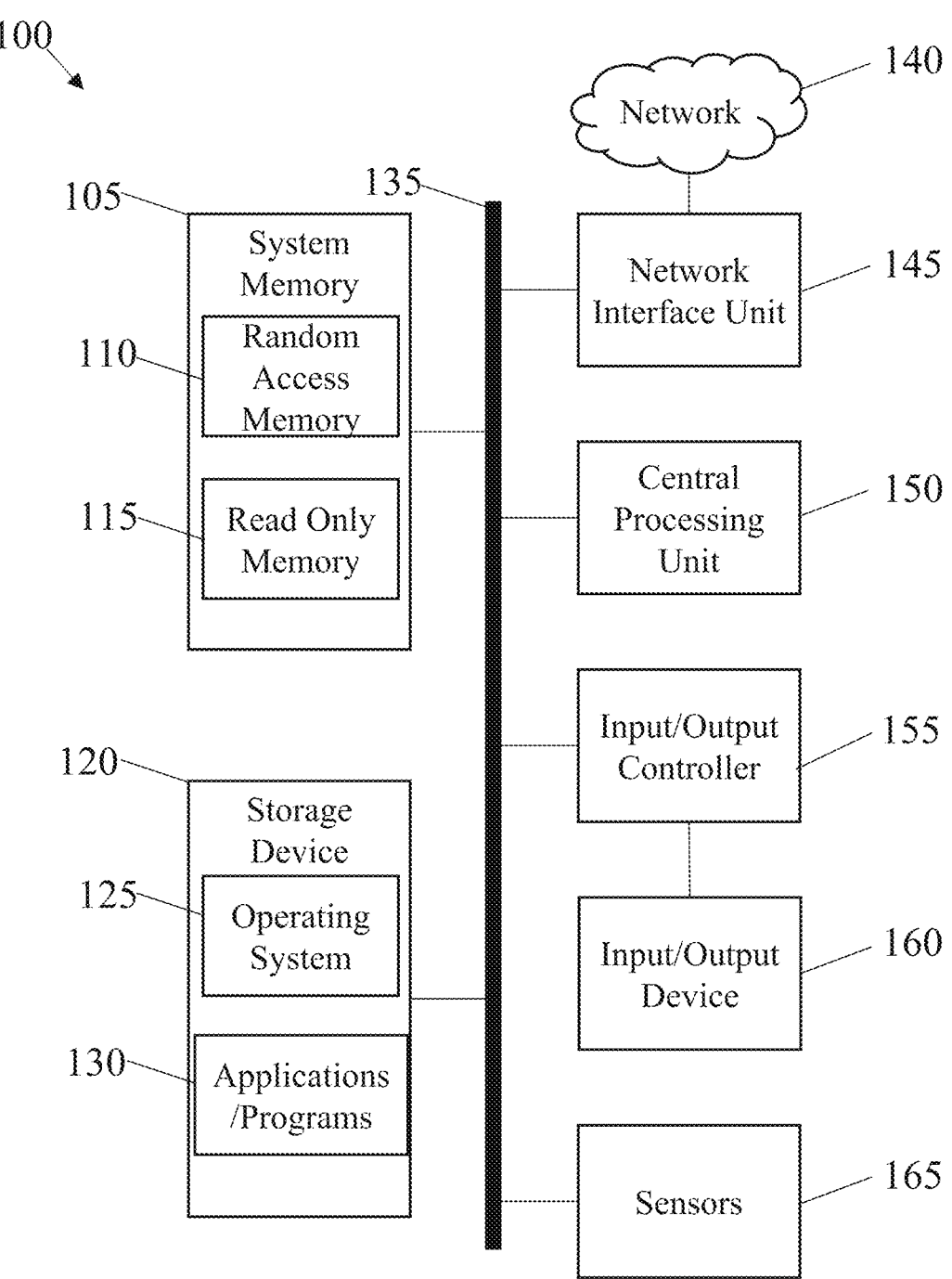
FIG. 1 is an exemplary suitable computing environment in which the method described herein may be implemented with, according to one embodiment.

It is to be understood that the figures and descriptions of the present invention have been simplified to illustrate elements that are relevant for a clear understanding of the present invention, while eliminating, for the purpose of clarity, many other elements found in related systems and methods. Those of ordinary skill in the art may recognize that other elements and/or steps are desirable and/or required in implementing a method of treading a patient with respiratory illness. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Embodiments of the invention describe a method that places spirometry equipment in the PCP office and with an avatar to guide the testing, can collect hospital laboratory quality data without a trained technician in the PCP office. The data is then sent to a cloud server where it undergoes an automated interpretation strategy. Depending on the severity of the disease determined by the interpretation algorithm, the patient may be automatically referred to a pulmonologist for treatment guidance or management depending on the expressed comfort level of the PCP to manage specific disease levels.

Depending on the severity of the COPD, patients will be automatically referred for one of or a combination of several levels of automated management/monitoring including a communications regimen with healthcare tips, action plans that collect patient self-perception of health status with automated instruction responses, or physiologic data collection monitoring as measures of pulmonary status. The system also includes automated presentation of recommended medications for the PCP based on the severity of the disease.

First a system architecture will be described as an example embodiment for implementing a method for treating a patient with respiratory illness. Embodiments of the method for treating a patient with respiratory illness will at times involve one or more computing devices accessed by the patient, a patient caregiver, the PCP, a specialist, and medical support staff. In some aspects of the present invention, software executing the instructions provided herein may be stored on a non-transitory computer-readable medium, wherein the software performs some or all of the steps of the method when executed on a processor.

Aspects of the method for treating a patient with respiratory illness relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C#, Objective-C, Java, JavaScript, MATLAB, Python, PHP, Perl, Ruby, or Visual Basic. It is further understood that elements of the method for treating a patient with respiratory illness may be executed on any acceptable computing platform, including but not limited to a server, a cloud instance, a workstation, a thin client, a mobile device, an embedded microcontroller, a television, or any other suitable computing device known in the art.

Parts of the method for treating a patient with respiratory illness are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of the method for treating a patient with respiratory illness are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G, 4G/LTE, or 5G networks, Bluetooth®, Bluetooth® Low Energy (BLE) or Zigbee® communication links, or any other method by which one electronic device is capable of communicating with another.

In some embodiments, elements of the networked portion of the invention may be implemented over a Virtual Private Network (VPN).

FIG. 1 and the following discussion are intended to provide a brief, general description of a suitable computing environment in which the method for treating a patient with respiratory illness may be implemented. While the invention is described above in the general context of program modules that execute in conjunction with an application program that runs on an operating system on a computer, those skilled in the art will recognize that the invention may also be implemented in combination with other program modules.

Generally, program modules include routines, programs, components, data structures, and other types of structures that perform particular tasks or implement particular abstract data types. Moreover, those skilled in the art will appreciate that the invention may be practiced with other computer system configurations, including hospital or medical facility computer systems, hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

FIG. 1 depicts an illustrative computer architecture for a computer 100 for practicing the various embodiments of the method for treating a patient with respiratory illness. The computer architecture shown in FIG. 1 illustrates a conventional computer system, including a central processing unit 150 ("CPU"), a system memory 105, including a random-access memory 110 ("RAM") and a read-only memory ("ROM") 115, and a system bus 135 that couples the system memory 105 to the CPU 150. A basic input/output system containing the basic routines that help to transfer information between elements within the computer, such as during startup, is stored in the ROM 115. The computer 100 further includes a storage device 120 for storing an operating system 125, application/program 130, and data.

The storage device 120 is connected to the CPU 150 through a storage controller (not shown) connected to the bus 135. The storage device 120 and its associated computer-readable media provide non-volatile storage for the computer 100. Although the description of computer-readable media contained herein refers to a storage device, such as a hard disk or CD-ROM drive, it should be appreciated by those skilled in the art that computer-readable media can be any available media that can be accessed by the computer 100.

By way of example, and not to be limiting, computer-readable media may comprise computer storage media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

According to various embodiments of the method for treating a patient with respiratory illness, the computer 100 may operate in a networked environment using logical connections to remote computers through a network 140, such as TCP/IP network such as the Internet or an intranet. The computer 100 may connect to the network 140 through a network interface unit 145 connected to the bus 135. It should be appreciated that the network interface unit 145 may also be utilized to connect to other types of networks and remote computer systems.

The computer 100 may also include an input/output controller 155 for receiving and processing input from a number of input/output devices 160, including a keyboard, a mouse, a touchscreen, a camera, a microphone, a controller, a joystick, or other type of input device. Similarly, the input/output controller 155 may provide output to a display screen, a printer, a speaker, or other type of output device. The computer 100 can connect to the input/output device 160 via a wired connection including, but not limited to, fiber optic, Ethernet, or copper wire or wireless means including, but not limited to, Wi-Fi, Bluetooth, Near-Field Communication (NFC), infrared, or other suitable wired or wireless connections.

As mentioned briefly above, a number of program modules and data files may be stored in the storage device 120 and/or RAM 110 of the computer 100, including an operating system 125 suitable for controlling the operation of a networked computer. The storage device 120 and RAM 110 may also store one or more applications/programs 130. In particular, the storage device 120 and RAM 110 may store an application/program 130 for providing a variety of functionalities to a user. For instance, the application/program 130 may comprise many types of programs such as a word processing application, a spreadsheet application, a desktop publishing application, a database application, a gaming application, internet browsing application, electronic mail application, messaging application, and the like. According to an embodiment of the present invention, the application/program 130 comprises a multiple functionality software application for providing word processing functionality, slide presentation functionality, spreadsheet functionality, database functionality and the like.

The computer 100 in some embodiments can include a variety of sensors 165 for monitoring the environment surrounding and the environment internal to the computer 100. These sensors 165 can include a Global Positioning System (GPS) sensor, a photosensitive sensor, a gyroscope, a magnetometer, thermometer, a proximity sensor, an accelerometer, a microphone, biometric sensor, barometer, humidity sensor, radiation sensor, or any other suitable sensor. Physiological sensors such as pulse oximeters to measure the oxygen saturation levels in blood and heart rate monitors may be utilized. Other physiological sensors may include but are not limited to weight scales, weight scales with bioimpedance measurements of fluid, or devices for measuring hand grip strength, exhaled nitric oxide, forced oscillation impedance, temperature, and activity.

Now referring to FIG. 2, a method 200 for treating a patient with respiratory illness is presented according to one embodiment. All steps illustrated herein may be performed by any type of computing device described herein, such as computer 100 described above. The steps of method 200, as further explained below, involve receiving a set of screening spirometry test data measured by a spirometer, generating a first patient performance score based on the received set of screening spirometry test data, and generating one of a first high alert when the first patient performance score crosses a first threshold and a first low alert when the first patient performance score fails to cross the first threshold. Next, the method includes receiving a set of at-home physiological test data, generating a second patient performance score based on the received set of at-home physiological test data, generating one of a second high alert when the second patient performance score crosses a second threshold and a second low alert when the second patient performance score fails to cross the second threshold, receiving a set of at-home patient survey data entered by the patient, generating a third patient performance score based on the received set of at-home patient survey data, and generating one of a third high alert when the third patient performance score crosses a third threshold and a third low alert when the third patient performance score fails to cross the third threshold.

With reference to step 201 of method 200, computer 100 receives a set of screening spirometry test data measured by a spirometer. The set of screening spirometry test data may include for example data concerning the patient's lungs collected from the patient using a spirometer device. The spirometer device is configured to measure the patient's respiratory performance or performance of a particular breathing maneuver. The data composing the set of screening spirometry test data may include the measurements from the spirometer or other information collected in relation to the state of the patient's lungs, such as information received as patient or observer feedback. The spirometer can measure the volume of air a patient is able to breathe in and out, information such as, but not limited to:

Forced vital capacity (FVC): This is the maximum amount of air a patient can exhale after taking a deep breath. It is measured in liters and can provide information about a patient's lung function.

Forced expiratory volume (FEV1): This is the volume of air a patient can exhale in one second after taking a deep breath. It is measured in liters and can provide information about how well a patient's lungs are working.

Peak expiratory flow (PEF): This is the maximum speed at which a patient can exhale air. It is measured in liters per minute and can provide information about the severity of a patient's respiratory condition.

Forced expiratory flow (FEF50 or FEF25-75): This is the rate of airflow during the middle portion of a forced exhalation. It is measured in liters per second and can provide information about how well a patient's airways are working.

Slow vital capacity (SVC): This is the maximum volume of air a patient can exhale slowly after taking a deep breath. It is measured in liters and can provide information about a patient's lung function.

In addition the data may include information about the patient's breathing pattern, the patient's ability to follow a coached breathing maneuver, and for tracking the shape of their flow-volume curve. This information can be relied upon by the system to measure patient performance at the moment in time and track changes in lung function over time.

To receive this information, step 201 may be performed by a primary care physician (PCP), who is responsibility for extracting the set of screening spirometry test data from the patient. This administration of care from the PCP can be those at are typically the first point of contact for patients seeking medical care. This may include for example private practices (e.g. a solo or group practice that offers a range of services, such as preventative care, disease management, and minor procedures), a community health center (e.g. non-profit clinics that provide medical care to particular populations, such as underserved, urban or rural populations), hospitals (e.g. as outpatient clinics or as part of a hospitalist program), or a telemedicine practice that sees patients virtually. In an embodiment, once the test data is received, the set of screening spirometry test data is then uploaded to computer 100 and may then be analyzed by an artificial intelligence program, which is further explained below.

At step 202, computer 100 generates a first patient performance score based on the received set of screening spirometry test data. A first patient performance score is a numerical value assigned to represent the severity of the patient's respiratory illness as a result of the set of screening spirometry test data received. The first patient performance score may be calculated based on input from an artificial intelligence (AI) module or program. For example, once the set of screening spirometry test data is entered into computer 100 by a PCP, an AI program can interpret the data and output the first patient performance score. To calculate first patient performance score, the program may use machine-learning models and training data to output a score. The machine learning model used may involve an algorithmic model built from a historical, or a previously trained, datasets and apply that to a new dataset. For example, computer 100 may generate the first patient performance score by utilizing a database previously received sets screening spirometry test data and their respective calculated scores. The patient performance score may in certain embodiments be influenced by scores from similar patients or a predefined group of patients. In one embodiment, the lower the calculated first patient performance score is, the more severe their respiratory illness is. Furthermore, the AI module may be, in an embodiment, an AI-based Clinical Impression program.

With reference to step 203, the step of generating one of a first high alert when the first patient performance score crosses a first threshold and a first low alert when the first patient performance score fails to cross the first threshold is performed. In an embodiment, and without limitation, crossing the first threshold may include crossing above the threshold and in another embodiment, crossing the first threshold may include crossing below the threshold. As used herein, first threshold may be a specific value of the first patience performance score wherein the value of each score calculated is either above or below said that value. The first threshold represents the separation of score values that indicate the severity of the patient's respiratory condition and may be set by the AI program/module explained above. For example, if the first patient performance score is below the first threshold, then a first low alert is generated. For example, if the first patient's performance score is above a first threshold, then a first high alert is generated. A low alert may indicate that the patient's respiratory illness is below the threshold, and thus not as severe or concerning. On the other hand, a high alert indicates that the patient's respiratory illness is above the threshold and is more concerning. As a result of these low and high alerts, the patient may be referred to a different PCP or even a respiratory specialist such as a pulmonologist, which is someone who specializes and has more expansive knowledge about respiratory illness than a PCP. For example, if a low alert is generated, then the care of the patient may stay with their current PCP since their illness does not require more help or specialist knowledge, and the AI module may generate a communication transmitted to a primary care physician. Another example, if a high alert is generated, then the AI module may generate a communication transmitted to a respiratory specialist who may be able to provide more specific and specialized care and help to overcome the harsher illness or more complex health issue.

Figure 3:
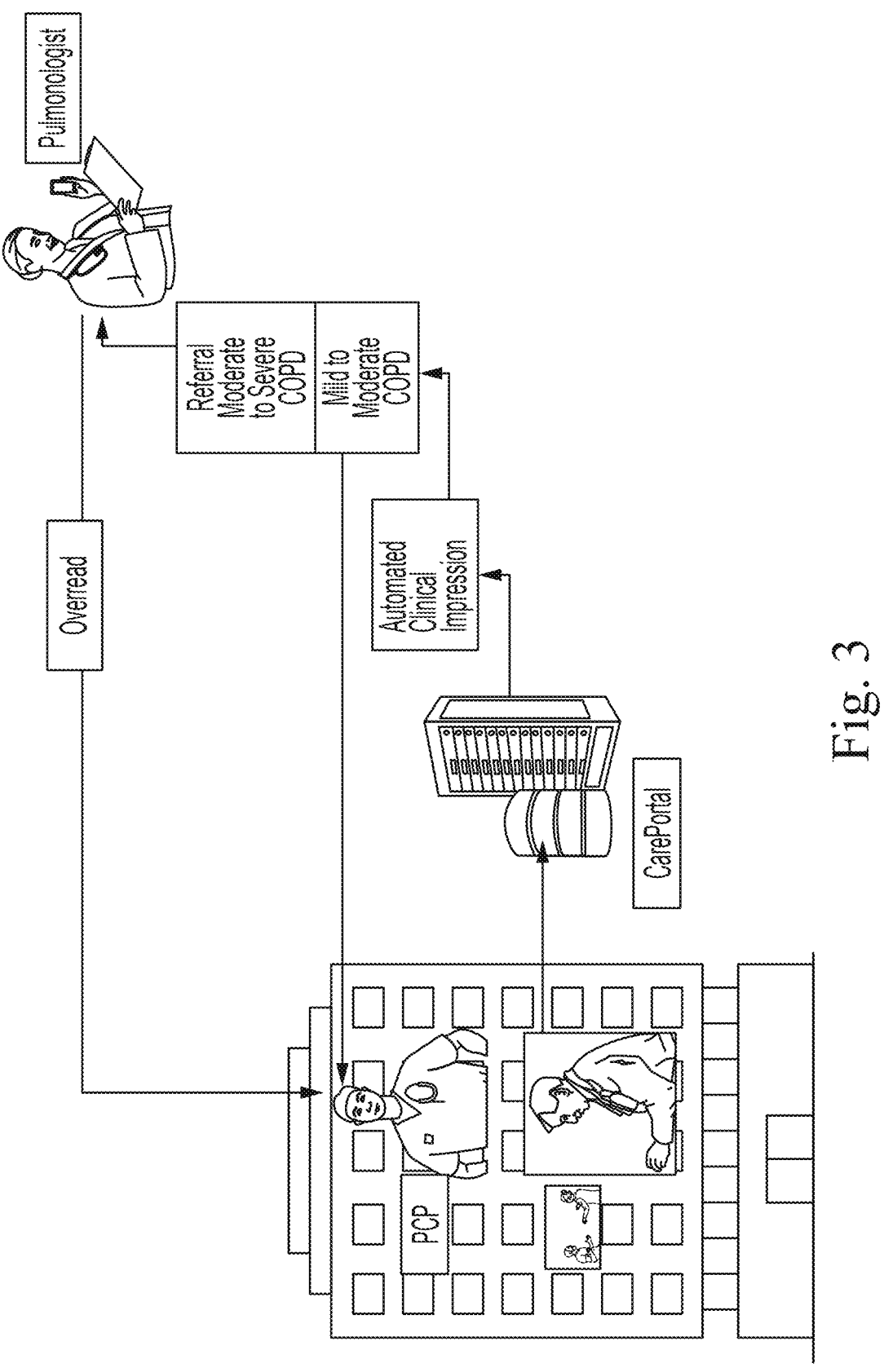
FIG. 3 is a diagram depicting part of a method for treating a patient with respiratory illness, according to one embodiment.

Now referring to FIG. 3, a diagram describing steps 201 to 203 of a method 200 for treating a patient with respiratory illness is shown according to one embodiment. Patient screening is performed by the primary care provider. This screening may be anything that includes initial readings of the patient, including spirometry readings, survey data from talking to the patient, or any other data described above in relation to set of screening spirometry test data. Next, the set of screening spirometry test data is uploaded to computer 100. In an embodiment, set of screening spirometry test data is uploaded to a sort of patient care portal, such as and without limitation, a CarePortal. Once uploaded, the data is analyzed by an AI based module, such as a Clinical Impression program. The analyzation includes step 202 of generating a first patient performance score, or an automated clinical impression score in the figure. Then in step 203, the first patient performance score is compared to the first threshold. First threshold may be a PCP specific chronic obstructive pulmonary disease (COPD) severity threshold. In one embodiment, if the score is above first threshold and generates a high alert, it may indicate moderate to severe COPD symptoms. In another embodiment, if the score is below first threshold and generates a low alert, it may indicate mild to moderate COPD symptoms. As a result of these alerts, the patient may either be referred to a specialist for their moderate to severe COPD symptoms, such as the pulmonologist, or the patient's care may stay managed by the PCP for the mild symptoms from the low alert generated. Furthermore, it may be possible in an embodiment for the pulmonology, or respiratory specialist, to provide oversight or overreading to the patient's care even if the patient stays in the care of the PCP.

Additionally, and still referring to FIG. 3, once the patient is referred to a PCP or respiratory specialist as a function of the first high or low alert, a care plan for that patient may be developed that may include at-home care, which is further explained throughout the rest of the steps in method 200. A patient care plan may include any set of instructions or data given to the patient by the PCP or respiratory specialist that instructs them how to treat their COPD or another respiratory illness. The PCP and pulmonologist may both edit or change patient care plan based on any of the data sets received herein.

Referring now back to FIG. 2, step 204 involves computer 100 receiving a set of at-home physiological test data according to one embodiment. At-home physiological test data may be any sort of data received at computer 100 that comes from the patient's home, or home computing device, that related to their respiratory health and its function. Set of at-home physiological test data may be any data and information concerning the patient's lungs collected from the patient in their own home, not in a PCP or respiratory specialist's office. The set of at-home physiological test data may be measured from a spirometer, or any other device capable of reading or detecting lung health. Spirometer may be any of the spirometers mentioned herein. Furthermore, and without limitation, set of at-home physiological test data may also include information manually entered into computer 100 by the patient or collected automatically. For example, and without limitation, at-home physiological data may include a spirometry reading, heart rate, weight, temperature, blood pressure, irregularities in breath that the patient has documented, presence of lung pain, or any other information that informs the healthcare professionals (the PCP and respiratory specialist) about the patient's current respiratory state without having to talk or chat through computer 100 or in person. Various types of at-home physiological data can be utilized to monitor the heal of various organ systems. Physiological data such as heart rate, blood pressure, electrocardiogram (ECG), and cardiac output can be used to monitor the cardiovascular system. Physiological data such as respiratory rate, oxygen saturation, and end-tidal carbon dioxide can be used to monitor the respiratory system. Physiological data such as electroencephalogram (EEG), electromyogram (EMG), and nerve conduction studies can be used to monitor the nervous system. Physiological data such as gastric acid secretion, intestinal motility, and absorption can be used to monitor the digestive system. Physiological data such as hormone levels, glucose levels, and insulin levels can be used to monitor the endocrine system. Physiological data such as urine output, urine concentration, and kidney function can be used to monitor the urinary system. Physiological data such as muscle activity, muscle fatigue, and muscle strength can be used to monitor the musculoskeletal system. Physiological data such as white blood cell count, cytokine levels, and antibody levels can be used to monitor the immune system.

At step 205, computer 100 generates a second patient performance score based on the received set of at-home physiological test data. A second patient performance score is a numerical value assigned to represent the severity of the patient's respiratory illness as a result of the set of at-home physiological test data received. Calculated similarly to the first patient performance score but with different historic and new datasets, the second patient performance scores may be calculated based on input from an artificial intelligence module, which may be any AI program or module described herein. For example, once the set of at-home physiological test data is entered into computer 100 by the patient in their home, an AI program will interpret the data and output the second patient performance score. To calculate the second patient performance score, the program may use machine-learning models and training data to output a score, as described above. The machine learning model used may involve an algorithmic model built from a historical or a previously trained dataset, applied to that new dataset. For example, computer 100 may generate the second patient performance score by utilizing a database of previously received sets of at-home physiological test data, from that patient alone or from a collection of multiple patients, and their respective calculated scores. In one embodiment, the lower the calculated second patient performance score is, the more severe the patient's respiratory illness is.

Furthermore, generating a third patient performance score may further include survey data generated by the patient. Survey data may include any questions or information answered by the patient that is voluntarily inputted into their computer 100. For example, a set of questions may be sent to the patient by the PCP, the respiratory specialist, or the AI program. The questions and information collected from the patient may be any type of input from the patient that is manually entered. The survey data may be the only data included in the calculation of the third patient performance score or may further be used along with a spirometer reading or any other respiratory-related data that can be collected at home.

Next, at step 206, the computer 100 generates one of a second high alert when the second patient performance score crosses a second threshold and a second low alert when the second patient performance score fails to cross the second threshold. The second threshold is a value set by the AI program that relates to the set of at-home physiological data. The second threshold may be further based on input provided by at least one of a primary care physician and a respiratory specialist. In one embodiment, and without limitation, crossing the second threshold means crossing above the threshold and in another embodiment, crossing the second threshold means crossing below the threshold. The second threshold acts similarly in a way to first threshold in that they represent the severity of the patient's respiratory illness but may be of a different value. However, the second threshold relates to the set of at-home physiological test data and second patient performance score. Each second patient performance score generated may be above or below the second threshold, which determines whether a second high alert or second low alert is generated. For example, if the second patient performance score is below the second threshold, then a second low alert is generated. Or for example, if the second patient performance score is above a second threshold, then a second high alert is generated. Further, a second low alert may indicate that the patient's respiratory illness is below the threshold, and thus not as severe or concerning. On the other hand, a second high alert may indicate that the patient's respiratory illness is above the threshold and is more concerning and may need emergency assistance. Second high or low alerts may be sent to any medical professional mentioned herein. As a result of these second low and high alerts, the patient may be referred to their PCP, respiratory specialist, pulmonologist or disease specialist. In another embodiment, for example, a second high alert may involve contacting emergency services, alerting the respiratory specialist that a change in a patient care plan is required, alerting the PCP of any issues, alerting the patient to contact their healthcare physician or emergency department, or issuing any other communication about the patient that's indicative of their respiratory health status.

The method 200 may comprise providing a physiological measurement device configured to measure patient physiological data remotely. A physiological measurement device, as used herein, is any device capable of measuring the ability of body parts or organs to function efficiently. In this case, the physiological data measured by the physiological measurement device may be any data related to the patient's respiratory health and their lung function or other organ system comorbidities. Physiological measurement device may include, without limitation, a pulse oximeter, a spirometer, a blood pressure monitor, a weight measurement device, or any other device capable of measuring the patient's physiological data. The physiologic device may include, without limitation, a GoSpiro, SpO2, BP, or the like. The device may be capable of measuring only one physiological datum, such as only heartbeat, or may be capable of measuring a multitude of physiological measurements. The physiological measurement device may be further receive a set of at-home physiological measurement data measured by the physiological measurement device. From this data, the physiological measurement device may then generate the second patient performance score further based on the received set of at-home physiological measurement data. Furthermore, second patient performance score may be calculated as a result of both the set of at-home physiological measurement data and the set of at-home physiological data described previously. In one embodiment, the physiological measurement device is communicatively connected to computer 100 so that the set of at-home physiological measurement data may be uploaded to the AI module.

Moreover, the physiological measurement device may be further configured to upload the patient test data, or the set of at-home physiological measurement data, to a remote server. The remote server may be any server described herein on computer 100. Once the data is uploaded to the server, it may then be compared to a clinical threshold generated by the AI program, also on computer 100. Clinical threshold indicates a value or boundary of data wherein the data collected is categorized either below or above the clinical threshold. After the data is compared to the clinical threshold, physiological measurement device may then be configured to generate a clinical alert as a result of the comparison between the data and the clinical threshold. Clinical threshold may be any of the thresholds mentioned herein, such as second threshold. Additionally, clinical threshold may be set by the AI program or by the PCP or respiratory specialist.

The method 200 may further comprise instructing the patient to perform a breathing maneuver via an avatar. This includes for example the techniques described in US Publication No. 2016/0249851 to Stenzler titled "Digitally Coached Spirometry System and Method", incorporated herein by reference. This breathing maneuver may include instructions for the patient on how to properly use a physiological measurement device. Instructions may include, without limitation, how long to breathe in and out for, number of breaths, quickness of breath, or any other instructions to help the patient obtain an accurate reading. Furthermore, the avatar may be any sort of image or module sent to the patient via computer 100 that visually shows the patient the instructions. For example, without limitation, avatar may be an instructional video for the patient, a clip of another person or animated person demonstrating the breathing maneuver, an animation instructing the patient, or anything similar. Furthermore, instructing the patient to repeat a breathing maneuver via an avatar may be based on a previous spirometer measurement. The AI program may be configured to generate an avatar to instruct the patient to do the breathing maneuver as a result of the patient's previous spirometer measurements. For example, if the spirometer previously detects data related to the deepness of the patient's breathe, then the avatar will instruct the patient to take many deep breaths to obtain an accurate reading of the problem to be reported to the PCP or respiratory specialist, if needed.

Figure 4:
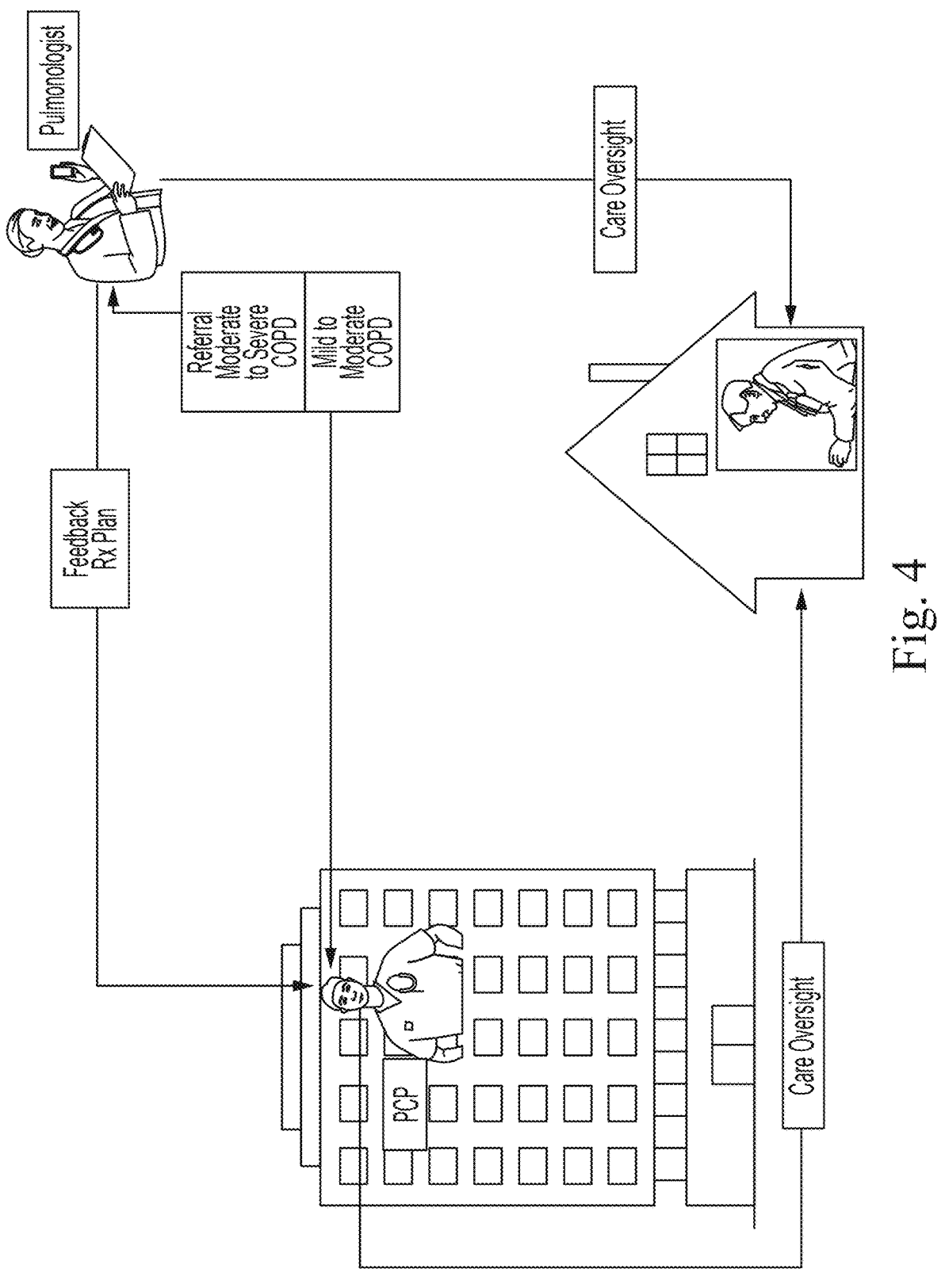
FIG. 4 is a diagram depicting part of a method for treating a patient with respiratory illness, according to one embodiment.

Now referring to FIG. 4, illustrated are steps 204 to 206 of a method 200 for treating a patient with respiratory illness. These steps include both the PCP and pulmonologist providing oversight to the patient from their own home. As stated above, the pulmonologist can assist the PCP with developing a patient care plan for patients that the PCP will manage. In another embodiment, the pulmonologist will develop the patient care plan for the patients they will be managing. Similar to the diagram shown in FIG. 3, the high alert indicates moderate to severe COPD symptoms while the low alert indicates mild to moderate symptoms. Depending on the severity of their COPD, patients may be sent home with physiologic measurement technology (e.g., pulse oximeter, spirometer, Blood Pressure device, weight scale, etc.) or just a digital care plan; physiological measurement device is further explained below.

Referring back again to FIG. 2, the next step 207 includes the computer 100 receiving a set of at-home patient survey data entered by the patient according to one embodiment. At-home patient survey data may be any sort of data received at computer 100 that comes from the patient's home, or home computing device, as a result of a survey or questions related to their respiratory health. Set of at-home patient survey data may be any data and information concerning the patient's respiration that is manually entered into computer 100 by the patient in their own home remotely, not in a medical office or with a medical professional. Furthermore, any survey data may include specific questions or information that the PCP or respiratory specialist send to the patient. For example, and without limitation, set of at-home patient survey data may include data such as questions from the PCP about how the patient is currently feeling, instant messages between the patient and the respiratory specialist, a questionnaire about the side effects of a new medication or treatment, a weekly survey sent out by a medical professional about the patient's respiration, or anything similar. Questions may include for example, Are you experiencing any shortness of breath or difficulty breathing? Do you have a cough, and if so, is it dry or productive (producing phlegm or mucus)? Are you experiencing any chest pain or tightness? Do you have a fever or chills? Have often have you smoked or used tobacco products in the last 5 days? Have you recently been exposed to any environmental irritants or pollutants, such as air pollution or secondhand smoke? Have you traveled recently, particularly to areas with high levels of air pollution or respiratory illness outbreaks? Have your allergies been acting up? Are you depressed or under any particular type of stress at this time? Moreover, the survey data may not only involve the patient answering questions or the like, but may include manually uploaded data from other devices, such as a spirometer, scale, or heart monitor reading or anything relating to the patient's respiratory health.

At step 208, computer 100 then generates a third patient performance score based on the received set of at-home patient survey data according to one embodiment. A third patient performance score is a numerical value assigned to represent the severity of the patient's respiratory illness as a result of the at-home patient survey data received. Calculated similarly to the first and second patient performance score but with different historic and new datasets, the third patient performance score may be calculated based on input from an artificial intelligence module, which may be any AI program or module described herein. For example, once the set of at-home patient survey data is entered into the computer 100 by the patient in their home, an AI program will interpret the data and output the third patient performance score. Third patient performance score may be calculated using machine-learning models or any other method used on an AI program to calculate such a score. For example, the computer 100 may generate the third patient performance score by utilizing a database of previously received sets of at-home patient survey data, from that patient alone or from a collection of multiple patients, and their respective calculated scores. In an embodiment, the higher the calculated third patient performance score is, the more severe the patient's respiratory illness is.

At step 209, the computer 100 generates one of a third high alert when the third patient performance score crosses a third threshold and a third low alert when the third patient performance score fails to cross the third threshold according to one embodiment. The third threshold is a value set by the AI program that relates to the set of at-home patient survey data. The third threshold may be further based on input provided by at least one of a primary care physician and a respiratory specialist. In one embodiment, and without limitation, crossing the third threshold may include crossing above the threshold and in another embodiment, crossing the third threshold may include crossing below the threshold. Third threshold is calculated or set further based on the set of at-home patient survey data and third patient performance score. Each third patient performance score generated may be above or below the third threshold, which determines whether a third high alert or third low alert is generated. For example, and without limitation, the third patient performance score is below the third threshold, then a third low alert is generated. For example, and without limitation, if the third patient performance score is above a third threshold, then a third high alert is generated. Further, a third low alert may indicate that the patient's respiratory illness is below the third threshold, and thus not as severe or concerning. On the other hand, a third high alert may indicate that the patient's respiratory illness is above the threshold and is more concerning and may need emergency assistance. In one embodiment, the third low alert may generate a communication transmitted to the patient. This communication may be, without limitation, telling the patient to schedule an appointment with their PCP or pulmonologist or disease specialist, an adjustment for their patient care plan that is automated, or any other communication the help improve or help the patient as a result of the alert without the direct communication of a medical professional. In another embodiment, the third high alert may generate a communication transmitted to the patient and at least one of a primary care physician and a respiratory specialists. For example, but without limitation, the PCP or respiratory specialist may adjust the patient's care plan, refer them to another specialist, contact emergency services for the patient, or any other communication involving a medical professional.

Figure 5:
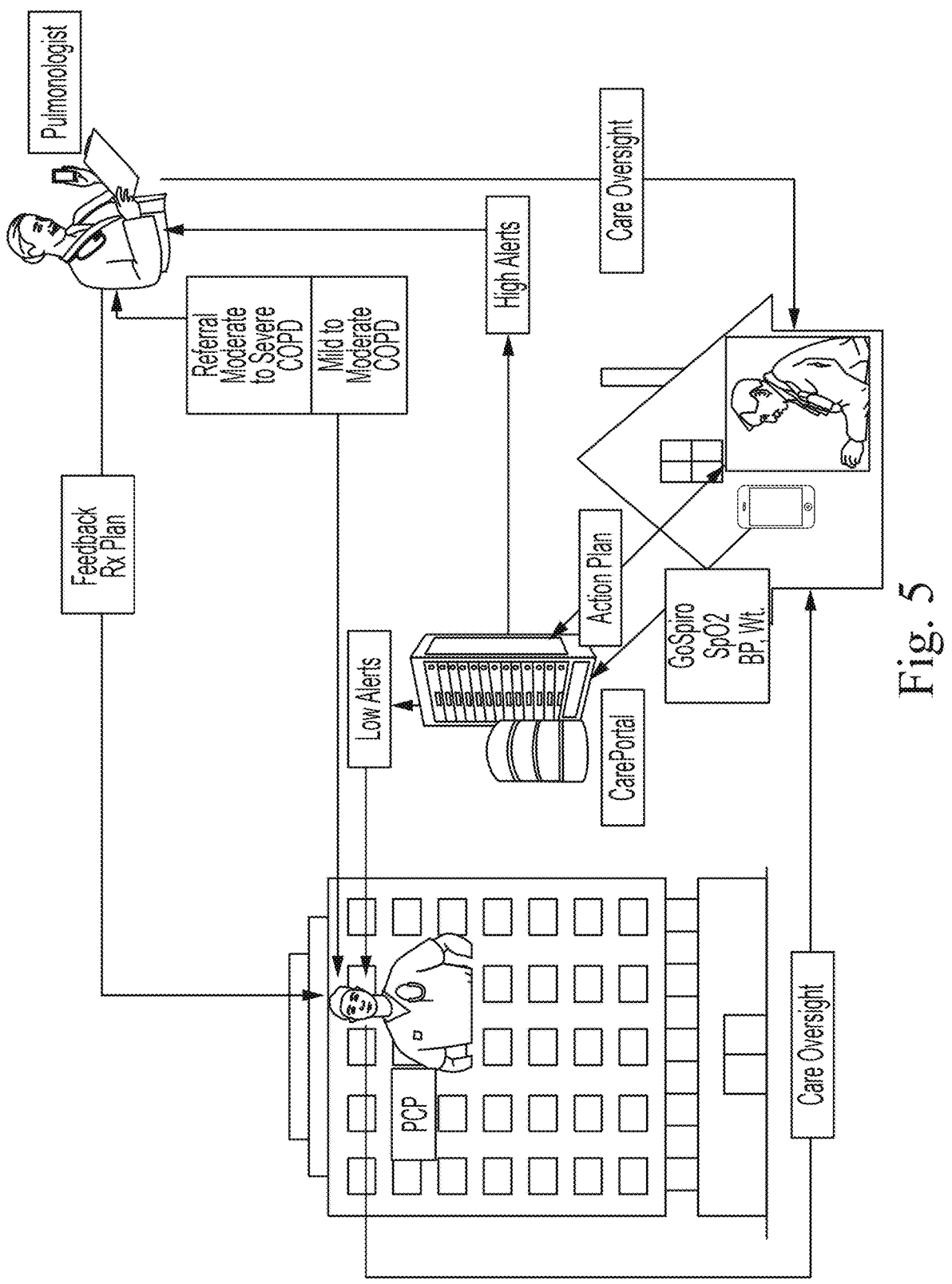
FIG. 5 is a diagram depicting part of a method for treating a patient with respiratory illness, according to one embodiment.
Figure 6:
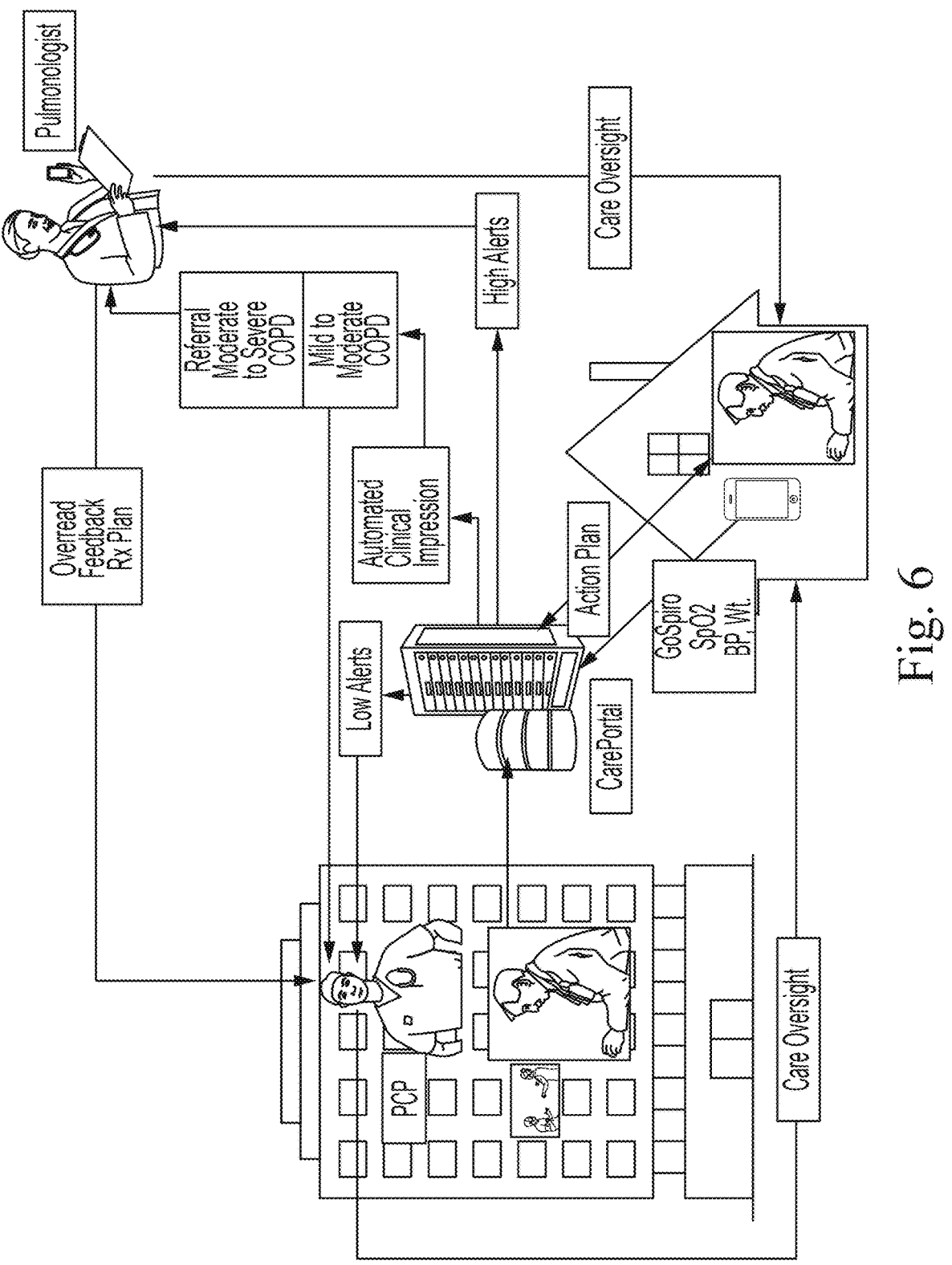
FIG. 6 is a diagram depicting part of a method for treating a patient with respiratory illness, according to one embodiment.

FIG. 5 depicts steps 207 to 209 of method 200 for treating a patient with respiratory illness are shown according to one embodiment. FIG. 6 depicts the of method 200 from steps 201 to 209 according to one embodiment, depicting the overall oversight of the PCP and pulmonologist over the patient, as well as computer 100 and the AI program used to develop and calculate steps in method 200. Patients may be monitored at home with a combination of physiologic measurements as explained above. In an embodiment, automated alerts generated from the results of the measurements or self-perception questions, are either sent to the PCP or pulmonologist based on who is managing the patient and the agreed alert threshold for each. The figure lays out the steps including the low and high alerts and which respective medical professional it will be sent to.

Method 200 may further include generating a z-score for the patient. In spirometry, a Zscore is a statistical measure used to evaluate a patient's lung function test results. A Zscore is a measure of how many standard deviations a patient's test result is from the average or expected result for someone of the same age, height, sex, and race/ethnicity. In other words, a Zscore indicates how much a patient's test result deviates from the average or expected result for someone with similar demographic characteristics. A Zscore of 0 means the test result is exactly average, a Zscore of +1 means the test result is one standard deviation above average, and a Zscore of −1 means the test result is one standard deviation below average. Using Zscores can be helpful in interpreting spirometry results because it allows for the comparison of an individual's test results with a large population of people with similar demographic characteristics. This helps to account for natural variations in lung function due to factors such as age, height, sex, and race/ethnicity. A Zscore of less than −1.645 or greater than +1.645 is generally considered abnormal and may indicate the presence of lung disease. If a patient's spirometry test results yield a Zscore outside of the normal range, further testing or medical evaluation may be necessary to determine the cause of the abnormal results and to develop an appropriate treatment plan. Patient's data may include any of the data sets mentioned herein, including set of screening spirometry test data, set of at-home physiological test data, set of at-home patient survey data, or any other datasets related to the patient's respiratory health. Zscore may be generated by AI program or module and may be calculated similar to the other scores calculated herein. A reference population for generating the Zscore may be solely based on previous measurements from the patient only, not a database including information from other patients. In one embodiment, computer 100 and/or AI program may generate an alert when the calculated Zscore falls below a Zscore threshold. The Zscore threshold may be a value in which once the Zscore falls below that value, the patient's respiratory health may be concerning and need the attention of a medical professional. In one embodiment, the Zscore threshold is based on a patient-specific baseline, and not other patient's data. In other words, the Zscore can be calculated based solely on the patient's historical data, not population historical data. In one embodiment, the Zscore can be rely on the patient's historical data and population data, while the patient's historical data is weighted to rely such that the Zscore relies heavily or even mostly on the patient's historical data. For example, the patient's historical data can be weighted to represent 10, 20, 30, 40, 50, 60, 70 percent or more of the population. In another embodiment, method 200 may further include generating a Zscore for the patient and then generating an alert when it falls below a Zscore threshold a plurality of times over a plurality of days, rather than just producing one reading one time.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating a patient with respiratory illness, the method comprising:

training a machine-learning model utilizing a database of previously received sets of screening spirometry test data and their respective calculated performance scores;

instructing the patient to perform a breathing maneuver via an animated avatar which demonstrates the breathing maneuver, wherein the animated avatar is generated by an artificial intelligence module;

receiving a current set of screening spirometry test data measured by via a spirometer by the patient following the breathing maneuver instructions;

generating a first patient performance score using the trained machine-learning model based on the received set of current screening spirometry test data;

generating one of a first high alert when the first patient performance score crosses a first threshold and a first low alert when the first patient performance score fails to cross the first threshold;

receiving a current set of at-home physiological test data;

generating a second patient performance score based on the received set of current at-home physiological test data;

generating one of a second high alert when the second patient performance score crosses a second threshold and a second low alert when the second patient performance score fails to cross the second threshold;

receiving a set of current at-home patient survey data entered by the patient;

generating a third patient performance score based on the received set of current at-home patient survey data; and generating one of a third high alert when the third patient performance score crosses a third threshold and a third low alert when the third patient performance score fails to cross the third threshold.

2. The method of claim 1, wherein at least one of the first, second and third thresholds are set by an the artificial intelligence module.

3. The method of claim 1, wherein at least one of the first, second and third patient performance scores are calculated based on input from an the artificial intelligence module.

4. The method of claim 1, wherein the received set of current at-home physiological test data is measured from a spirometer.

5. The method of claim 1, wherein the first or second low alert generates a communication transmitted to a primary care physician.

6. The method of claim 1, wherein the first or second high alert generates a communication transmitted to a respiratory specialist.

7. The method of claim 1, wherein the third performance score low alert generates a communication transmitted to the patient and or the physician.

8. The method of claim 1, wherein the third performance score high alert generates a communication transmitted to the patient and at least one of a primary care physician and a respiratory specialists.

9. The method of claim 1, wherein the second threshold is based on input provided by at least one of a primary care physician and or a respiratory specialist.

10. The method of claim 1 further comprising: providing a physiological measurement device configured to measure patient physiological data remotely, receiving a set of at-home physiological measurement data measured by the physiological measurement device, and generating the second patient performance score further based on the received set of at-home physiological measurement data.

11. The method of claim 10, wherein the physiological measurement device includes a pulse oximeter.

12. The method of claim 10, wherein the physiological measurement device includes a spirometer.

13. The method of claim 10, wherein the physiological measurement device includes a blood pressure monitor.

14. The method of claim 10, wherein the physiological measurement device includes a weight measurement device.

15. The method of claim 10, wherein the physiological measurement device is configured to:

upload the patient test data to a remote server; and generate a clinical alert by comparing the patient test data to a clinical threshold generated by the artificial intelligence program.

16. The method of claim 1, wherein the step of generating a third patient performance score is further based on survey data generated by the patient.

17. The method of claim 1 further comprising: instructing the patient to repeat a breathing maneuver via an avatar based on a previous spirometer measurement.

18. The method of claim 1 further comprising: generating a Zscore for the patient and generating an alert when it falls below a Zscore threshold, wherein a reference population for generating the Zscore is solely based on previous measurements from the patient only.

19. The method of claim 18, where in the Zscore threshold is based on a patient-specific baseline.

20. The method of claim 1 further comprising: generating a Zscore for the patient and generating an alert when it falls below a Zscore threshold a plurality of times over a plurality of days.

21. The method of claim 1, wherein crossing the first or second threshold comprises crossing above the threshold.

22. The method of claim 1, wherein crossing the first or second threshold comprises crossing below the threshold.

* * * * *